United States Patent [19]

Seshimoto et al.

[11] Patent Number: 4,783,251

[45] Date of Patent: Nov. 8, 1988

[54] IONIC ACTIVITY MEASURING DEVICE

[75] Inventors: Osamu Seshimoto; Akira Yamaguchi; Yoshio Saito, all of Asaka, Japan

[73] Assignee: Fuji Photo Film Co., Ltd., Kanagawa, Japan

[21] Appl. No.: 945,644

[22] Filed: Dec. 23, 1986

[30] Foreign Application Priority Data

Dec. 28, 1985 [JP] Japan .............................. 60-204699[U]
Dec. 28, 1985 [JP] Japan .................................. 60-299274
Dec. 28, 1985 [JP] Japan .................................. 60-299275
Mar. 18, 1986 [JP] Japan .............................. 61-39425[U]
Mar. 18, 1986 [JP] Japan .............................. 61-39426[U]
Mar. 19, 1986 [JP] Japan .................................. 61-61874

[51] Int. Cl.$^4$ ........................................... G01N 27/26
[52] U.S. Cl. ..................................... 204/412; 204/416; 204/435; 422/98
[58] Field of Search ............... 204/416, 418, 419, 435; 422/98

[56] References Cited

U.S. PATENT DOCUMENTS 4,171,246 10/1979 Hamblen et al. ................... 204/1 T
4,273,639 6/1981 Gottenmeier ....................... 204/416
4,437,970 3/1984 Kitajima et al. ................... 204/435

Primary Examiner—John F. Niebling
Assistant Examiner—Kathryn Gorgos
Attorney, Agent, or Firm—Jules E. Goldberg

[57] ABSTRACT

An ionic activity measuring device comprises ion selective electrodes, porous liquid distributing members for distributing a reference solution and a sample solution to the ion selective electrodes, a frame for housing the ion selective electrodes and the porous liquid distributing members and provided with a pair of liquid feed holes for feeding the reference solution and the sample solution to the porous liquid distributing members, and a porous bridge for achieving electrical conduction between the reference solution and the sample solution fed in drops to the liquid feed holes. The porous bridge is disposed in a recess formed in the surface of the frame so that the depth of the recess is not smaller than the height of the porous bridge. End portions of the porous liquid distributing members are protruded to regions under the liquid feed holes so that the fed solutions may enter from side faces of the end portions. The porous bridge may extend at positions deviated from centers of the liquid feed holes. The frame may be provided with holes for insertion of potential measuring probes, and air discharging holes.

5 Claims, 20 Drawing Sheets

F I G. 12
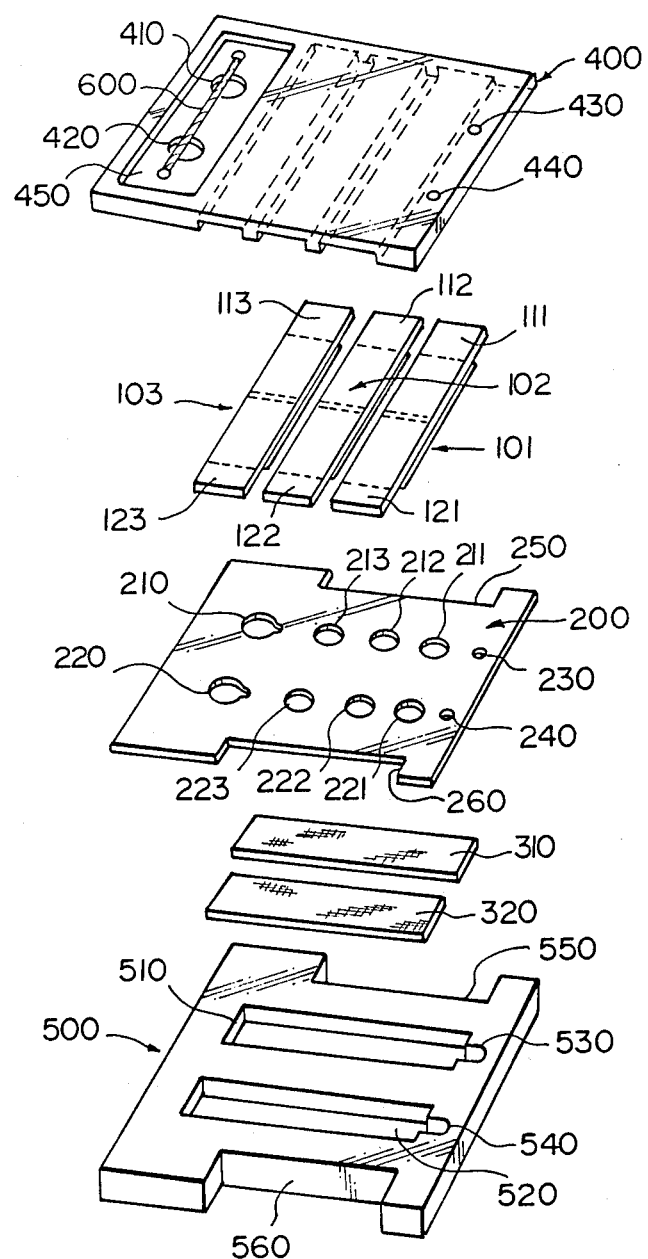

IONIC ACTIVITY MEASURING DEVICE

BACKGROUND OF THE INVENTION

1. Field of the Invention

This invention relates to an ionic activity measuring device for quantitatively analyzing the activity or concentration of a specific ion contained in an aqueous liquid sample, for example, a wine, a beverage, service water, and in particular a body fluid (blood, urine, saliva or the like), by potentiometry.

2. Description of the Prior Art

As disclosed in, for example, Japanese Unexamined Patent Publication Nos. 58(1983)-211648, 59(1984)-30055 and 60(1985)-155960, there have been proposed slide type ionic activity measuring devices for receiving a liquid sample fed in drops and measuring the activity of a specific ion contained in the sample.

In the ionic activity measuring devices as disclosed in Japanese Unexamined Patent Publication Nos. 58(1983)-211648 and 60(1985)-155960, multiple sets of ion selective electrode pairs respectively having an ion selective layer selectively responding to a predetermined ion are provided as the outermost layer. The lower sections of the ion selective electrode pairs are secured to a lower supporting frame, and the upper sections thereof are covered by a water-impermeable member layer provided with liquid receiving through holes at the positions corresponding to the respective electrodes of the ion selective electrode pairs, at least one liquid receiving through hole being formed for each of the ion selective electrodes. By means of a pair of porous liquid distributing members formed of a cotton bandage cloth, a polyester mesh or the like are disposed on the waterimpermeable member layer so that each of the porous liquid distributing members makes each set of the liquid receiving through holes corresponding to the respective member electrodes of the ion selective electrode pairs, are communicated with each other. Also, an upper frame provided with a pair of liquid feed holes (i.e. liquid droplet holes) respectively communicating with the respective porous liquid distributing members is disposed on the pair of porous liquid distributing members to match the lower supporting frame. A porous bridge formed of twisted fiber yarn or the like for achieving liquid junction, thus electrical conduction, between a sample solution fed in drops to one of the pair of the liquid droplet holes and a reference solution fed in drops to the other thereof is disposed, usually, on the pper frame.

In the case where the ionic activity measuring device having the aforesaid configuration is provided with, for example, multiple sets of the ion selective electrode pairs responding respectively to $Na^+$, $K^+$, and $Cl^-$ ions, drops of a reference solution having known activity values of these ions are fed to one of the pair of the liquid droplet holes, and drops of a sample solution wherein the activity values of these ions are unknown are fed to the other of the pair of the liquid droplet holes. The reference solution and the sample solution penetrate through the porous liquid distributing members to the corresponding ion selective electrodes via the liquid receiving holes. On the other hand, the reference solution and the sample solution contact each other to achieve a liquid-junction near the middle of the porous bridge (hereinafter often referred to simply as the bridge), and electrical conduction is effected between the two solutions. As a result, a potential difference proportional to the difference in activity of each ion between the reference solution and the sample solution arises between the electrodes of each ion selective electrode pair. By measurement of the potential differences, the activity values of the $Na^+$, $K^+$, and $Cl^-$ ions contained in the sample solution can be determined simultaneously or sequentially based on the measured values and calibration curves determined in advance from the activity values of the ions in the standard solution (by use of the Nernst equation).

With the aforesaid ionic activity measuring device, it is possible to measure the ionic activity values of a plurality of ions simply by feeding drops of the sample solution and the reference solution just once. Therefore, the ionic activity measuring device is very advantageous for analysis of an aqueous liquid sample, particularly for clinical analysis of a sample such as blood taken from the human body.

In the conventional ionic activity measuring device, the porous bridge is normally disposed on the upper surface of the upper frame in the vicinity of the liquid feed holes. Therefore, when a plurality of the ionic activity measuring devices are stacked and subjected to packaging, inspection or operation for measurement, the porous bridge of the ionic activity measuring device is often damaged or removed by the edges of the adjacent ionic activity measuring device placed on the upper side. The porous bridge is also readily damaged by a liquid feed instrument such as a pipette.

The primary object of the present invention is to provide an ionic activity measuring device wherein the time taken for a sample solution or a reference solution to arrive at the electrode surfaces is short so that the time required for ionic activity measurement is shortened, adverse effects of hemolysis of a whole blood sample solution are eliminated, and ionic activity measurement is not adversely affected by bubbles generated when a fed solution contacts the porous liquid distributing members.

Another object of the present invention is to provide an ionic activity measuring device wherein a sample solution and a reference solution fed in drops from liquid feed holes are allowed to smoothly permeate through porous liquid distributing members and quickly arrive at ion selective electrode pairs, and the solutions are fed reliably to the surfaces of ion selective electrodes by eliminating air confinement.

The specific object of the present invention is to provide an ionic activity measuring device which eliminates adverse effects of hemolysis of a whole blood sample solution and accurately measures ionic activity of the $K^+$ ion (potassium ion).

The present invention provides an ionic activity measuring device comprising:

(i) at least one pair of sheet-like ion selective electrodes provided with ion selective layers on their surfaces and electrically isolated from each other, (ii) at least one pair of porous liquid distributing members for feeding a reference solution and a sample solution respectively to said ion selective layers of said ion selective electrodes, (iii) a frame for housing said ion selective electrodes and/or said porous liquid distributing members therein and provided with a pair of liquid feed holes respectively disposed above said porous liquid distributing members for feeding said reference solution and said sample solution independently of each other to said porous liquid distributing members, and (iv) a porous bridge for achieving electrical conduction between said reference solution and said sample solution fed to said pair of the liquid feed holes, wherein the improvement comprises disposing said porous bridge in a recess formed in the upper surface of said frame, and adjusting the depth of said recess to a value not smaller than the height of said porous bridge.

With the ionic activity measuring device in accordance with the present invention, wherein the porous bridge does not project above the surface of the frame, another measuring device, a pipette or the like does not readily come into contact with the bridge. Therefore, it is possible to prevent the bridge from being damaged or removed, and to efficiently measure ionic activity.

The present invention also provides an ionic activity measuring device comprising the aforesaid members (i) to (iv), wherein the improvement comprises protruding an end portion of at least either one of said porous liquid distributing members to a part of a region under the corresponding liquid feed hole, whereby said reference solution or said sample solution is allowed to enter from the side face of said end portion.

With the second mentioned ionic activity measuring device in accordance with the present invention, wherein at least either one of the porous liquid distributing members is protruded to the region under the corresponding liquid feed hole, it is possible to prevent hemolysis of a whole blood sample solution and to eliminate bubbles contained in a fed solution. This device is suitable particularly for ionic activity measurement of whole blood.

In the second mentioned ionic activity measuring device in accordance with the present invention, "protruding" and "facing" embrace also the case where the liquid feed hole and the porous liquid distributing member meet each other only at a part of the side face of the end portion of the porous liquid distributing member. The shape of the end portion of the porous liquid distributing member (the shape on a projected plane as viewed normal to the liquid distribution advance direction) is not limited, and may be a linear shape, a circular arc shape (convex or concave), a curvilinear shape, or a shape constituting a part of a polygon (e.g. a hexagon or a octagon).

Also, end portions of two or more porous liquid distributing members may be disposed to face the region under the corresponding liquid feed hole.

In the case where the porous liquid distributing members are formed of a woven fabric or a knitted fabric having comparatively small interstices, for example, a cotton bandage cloth, cotton gauze, PET gauze or a cotton tricot, or a non-woven fabric or filter paper having small continuous pores and constituted by cotton fiber, regenerated cellulose fiber or synthetic polymer fiber, it takes a comparatively long time for a sample solution of relatively high viscosity to penetrate through the porous liquid distributing members when the sample solution is fed normal to the longitudinal direction of the fiber. Therefore, the configuration of the second mentioned ionic activity measuring device in accordance with the present invention, wherein the solution is fed mainly from cut ends of fibers of the porous liquid distributing members, is particularly advantageous for the porous liquid distributing members having small interstices or small continuous pores.

The liquid feed holes may be of any shape, such as a circle having a diameter within the range of approximately 1.5 mm to approximately 8 mm, or an ellipse or a polygon inscribed in the circle. When a plurality of the porous liquid distributing members are provided to face the corresponding liquid feed hole, they are spaced from each other at a distance within the range of approximately 1 mm to approximately 6 mm, preferably within the range of approximately 2 mm to approximately 3 mm, in the liquid distributing direction.

The present invention further provides an ionic activity measuring device comprising the aforesaid members (i) to (iv), wherein the improvement comprises extending said porous bridge through said pair of the liquid feed holes at positions deviated from centers of said liquid feed holes.

With the third mentioned ionic activity measuring device in accordance with the present invention, since the porous bridge is deviated from the centers of the liquid feed holes, drops of a reference solution or a sample solution may be fed to the center of each liquid feed hole so that the drop of liquid does not directly fall onto the porous bridge. Therefore, it is possible to eliminate loss of the solution caused by liquid repulsing by the bridge, and to prevent the bridge from being damaged by contact with an end of a pipette. As a result, it becomes possible to measure ionic activity accurately, quickly and easily.

The present invention also provides an ionic activity measuring device comprising:

(i) at least one ion selective electrode pair composed of solid-state electrodes provided on their surfaces with ion selective layers selectively responding to a predetermined ion, (ii) at least one pair of liquid distributing members for feeding a reference solution and a sample solution respectively to said ion selective layers of said ion selective electrode pair, (iii) a frame for supporting therein said ion selective electrode pair and said liquid distributing members and provided with a pair of liquid feed holes for feeding said reference solution and said sample solution independently of each other to said liquid distributing members, and (iv) a bridge for achieving electrical conduction between said reference solution and said sample solution fed to said pair of the liquid feed holes, wherein the improvement comprises providing said frame with potential measurement holes for allowing potential measuring probes to be inserted therethrough from the exterior to contact terminal sections of said ion selective electrode pair.

With the fourth mentioned ionic activity measuring device in accordance with the present invention, wherein the ion selective electrode pair is supported inside of the frame and the frame is provided with the potential measurement holes (i.e. through holes for insertion of potential measuring probes) communicating with the exterior, potential measurement can be conducted by inserting potential measuring probes from the exterior into the holes until the probes contact terminal sections of the ion selective electrode pair, and therefore it is possible to strengthen supporting of the terminal sections of the ion selective electrode pair and to prevent the ion selective electrode pair from being bent or damaged. Also, since the frame need not be partly cutaway for exposing the terminal sections of the ion selective electrode pair, it is possible to increase the strength of the frame, and consequently the strength of the ionic activity measuring device.

The present invention further provides an ionic activity measuring device comprising the members (i) to (iv) just mentioned above, wherein the improvement comprises providing a supporting section of said frame, where said frame supports said liquid distributing members, with air discharging holes for making said supporting section of said frame for said liquid distributing members communicating with the exterior at positions spaced from said liquid feed holes.

With the fifth mentioned ionic activity measuring device in accordance with the present invention, the air discharging holes are formed for making the supporting section of the frame for the liquid distributing members communicating with the exterior at positions of said supporting section remote from the liquid feed holes. Therefore, when a reference solution and a sample solution are independently fed from the liquid feed holes to the liquid distributing members, air in the liquid distributing members is pushed by the solutions and discharged through the air discharging holes to the exterior, so that the solutions smoothly permeate through the liquid distributing members. Accordingly, the solutions arrive quickly at the ion selective electrode pair without bubbles remaining midway along the liquid distributing members, and it becomes possible to conduct potential measurement quickly.

The present invention also provides an ionic activity measuring device comprising:

(i) at least three pairs of sheet-like ion selective electrodes provided with ion selective layers on their surfaces and electrically isolated from each other, (ii) at least one pair of porous liquid distributing members for feeding a reference solution and a sample solution respectively to said ion selective layers of said ion selective electrodes, (iii) a frame for housing said ion selective electrodes and said porous liquid distributing members therein and provided with a pair of liquid feed holes respectively disposed above said porous liquid distributing members for feeding said reference solution and said sample solution independently of each other to said porous liquid distributing members, and (iv) a porous bridge for achieving electrical conduction between said reference solution and said sample solution fed to said pair of the liquid feed holes, said at least three pairs of the sheet-like ion selective electrodes being disposed to stand side by side along said porous liquid distributing members, and said pair of the liquid feed holes being disposed in the vicinity of the center between the ion selective electrode pair positioned at one end and the ion selective electrode pair adjacent to said ion selective electrode pair positioned at said end, wherein the improvement comprises constituting said ion selective electrode pair adjacent to said ion selective electrode pair positioned at said one end, by a pair of potassium ion selective electrodes.

With the sixth mentioned ionic activity measuring device in accordance with the present invention, it is possible to prevent hemolysis of a whole blood sample solution and to accurately measure ionic activity of a potassium ion contained in the whole blood. In this ionic activity measuring device, the porous liquid distributing members are preferably disposed so that an end portion of at least one of the members faces the corresponding liquid feed hole as mentioned above with reference to the second mentioned ionic activity measuring device in accordance with the present invention.

BRIEF DESCRIPTION OF THE DRAWINGS

FIG. 12 is a perspective exploded view showing the embodiment of FIG. 11.

DESCRIPTION OF THE PREFERRED EMBODIMENTS

The present invention will hereinbelow be described in further detail with reference to the accompanying drawings.

Figure 1:
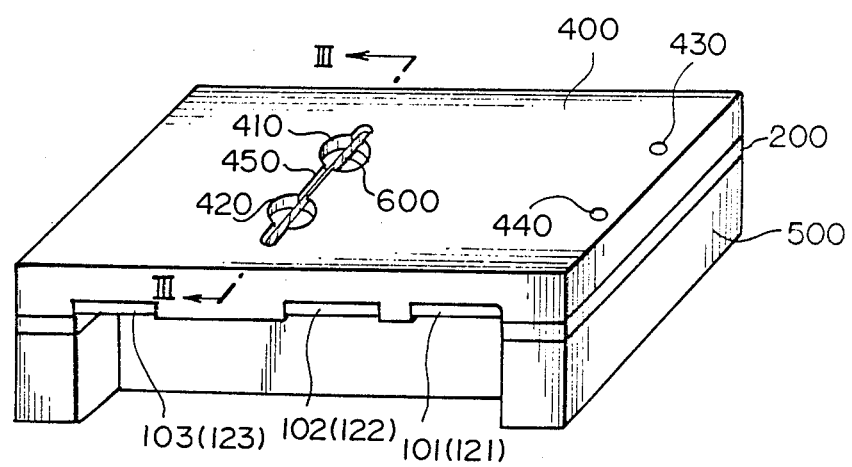
FIG. 1 is a perspective view showing an embodiment of the ionic activity measuring device in accordance with the present invention.
Figure 2:
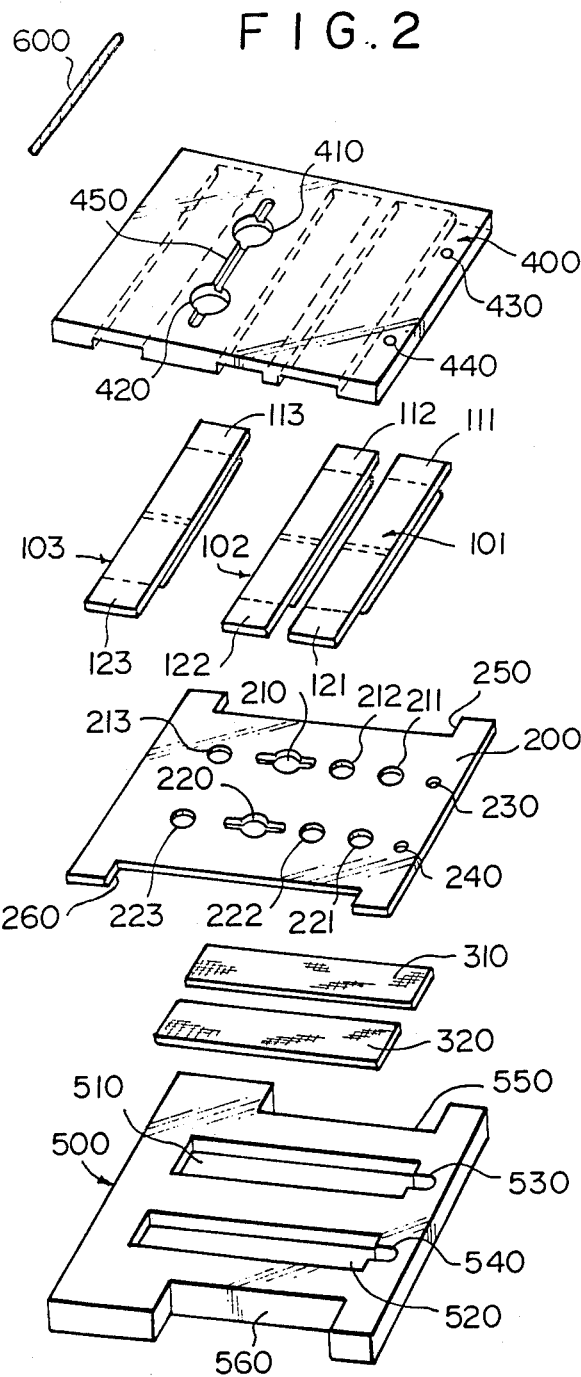
FIG. 2 is an exploded view showing the embodiment of FIG. 1.

Referring to FIGS. 1 and 2, an ionic activity measuring device comprises an upper frame half 400 and a lower frame half 500 formed of a plastic material. Between the upper frame half 400 and the lower frame half 500, there are housed an ion selective electrode pair 101 comprising ion selective electrodes 111 and 121 having ion selective layers of the same type on their surfaces and electrically isolated from each other, an ion selective electrode pair 102 comprising ion selective electrodes 112 and 122 having ion selective layers of the same type on their surfaces and electrically isolated from each other, an ion selective electrode pair 103 comprising ion selective electrodes 113 and 123 having ion selective layers of the same type on their surfaces and electrically isolated from each other, a water-impermeable member layer 200 having an adhesive layer on both surfaces, and a pair of porous liquid distributing members 310 and 320 formed of cotton and regenerated cellulose fiber nonwoven fabrics having continuous pores.

The upper frame half 400 is provided with a pair of liquid feed holes 410 and 420, and a recess 450 extending across the liquid feed holes 410 and 420. A porous bridge 600 formed of polyethylene terephthalate fibers or the like is housed and secured in the recess 450. The depth of the recess 450 is adjusted to such a value that the bridge 600 does not project from the upper surface of the upper frame half 400.

The water-impermeable member layer 200 disposed below the upper frame half 400 with the ion selective electrode pairs 101, 102, and 103 intervening therebetween is provided with through holes (liquid descent passages) 210 and 220 matched with the liquid feed holes 410 and 420, and through holes (liquid ascent passages) 211, 212, 213, 221, 222 and 223 respectively matched with portions of ion selective layer regions of the ion selective electrodes 111, 112, 113, 121, 122 and 123. Under the water-impermeable member layer 200, the porous liquid distributing member 310 is disposed to match with the through holes 210, 211, 212 and 213, and the porous liquid distributing member 320 is disposed to match with the through holes 220, 221, 222 and 223. The lower frame half 500 is provided with recesses (horizontal liquid passages) 510 and 520 having shapes capable of housing therein the porous liquid distributing members 310 and 320. Also, the upper frame half 400, the water-impermeable member layer 200, and the lower frame half 500 are respectively provided with a pair of through holes (air discharging holes) 430 and 440, a pair of through holes 230 and 240, and a pair of through holes 530 and 540, which constitute air discharging holes extending through the whole ionic activity measuring device. The ion selective electrode pairs 101, 102, and 103 are disposed with their ion selective layers facing down, and terminal sections of these ion selective electrode pairs are exposed at the lower surface of the ionic activity measuring device from a pair of cutaway regions 250 and 260 of the water-impermeable member layer 200, and a pair of cutaway sections 550 and 560 of the lower frame half 500.

In this embodiment, the ion selective electrode pairs 101, 102, and 103 are respectively provided with the ion selective layers selectively responding to, for example, $Cl^-$, $K^+$, and $Na^+$ ions. A reference solution having known ionic activity values of these ions is fed to the liquid feed hole 410, and a sample solution whose ionic activity values are unknown is fed to the liquid feed hole 420. The fed reference solution permeates through the porous liquid distributing member 310 via the liquid descent passage 210, and then passes through the liquid ascent passages 211, 212 and 213 to the ion selective layers of the ion selective electrodes 111, 112 and 113. On the other hand, the fed sample solution permeates through the porous liquid distributing member 320 via the liquid descent passage 220, and then passes through the liquid ascent passages 221, 222 and 223 to the ion selective layers of the ion selective electrodes 121, 122 and 123. Also, the reference solution and the sample solution come into contact with each other near the center of the bridge 600, thereby giving rise to electrical conduction therebetween. As a result, differences in potential corresponding to the differences in ionic activity of the $Cl^-$, $K^+$ and $Na^+$ ions between the reference solution and the sample solution are given rise to between the ion selective electrodes 111 and 121, between the ion selective electrodes 112 and 122, and between the ion selective electrodes 113 and 123. Accordingly, when potential measuring probes are inserted from below the cutaway regions 550 and 560 until they contact the terminal sections of the ion selective electrodes and the difference in potential across each ion selective electrode pair is measured, it is possible to measure the ionic activity of each ion contained in the sample solution.

Figure 3:
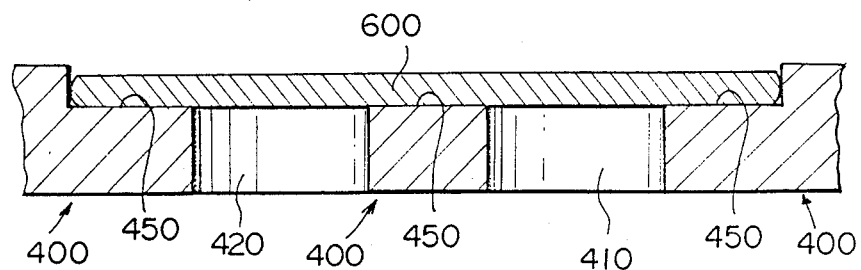
FIG. 3 is a partial vertical sectional view taken along line III—III of FIG. 1.

FIG. 3 is a vertical sectional view of the upper frame half 400 taken along line III-III of FIG. 1, and shows the relationship among the positions of the bridge 600, the liquid feed holes 410 and 420, and the recess 450 in the aforesaid embodiment. As shown in FIG. 3, since the depth of the recess 450 is larger than the height of the bridge 600 housed therein, the bridge 600 is maintained below the surface of the upper frame half 400. Therefore, it is possible to prevent the bridge 600 from readily coming into contact with the other ionic activity measuring device, an end of a pipette, or the like when the measuring devices are stacked or a solution is fed to the measuring device.

Figure 4:
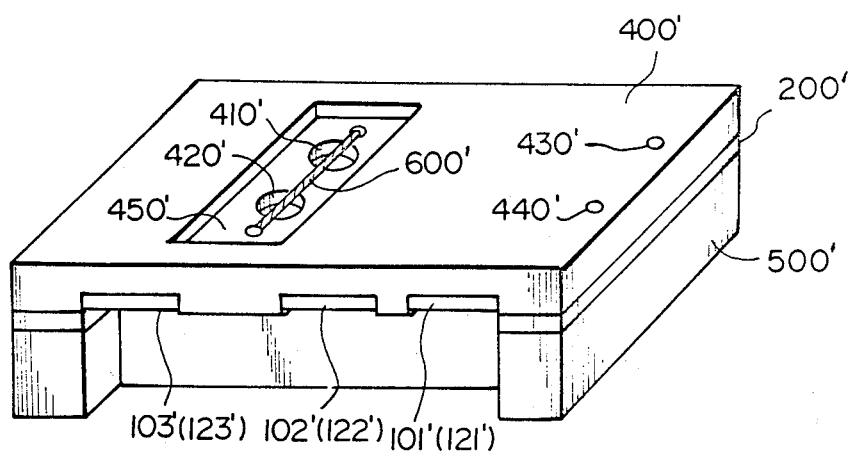
FIG. 4 is a perspective view showing another embodiment of the ionic activity measuring device in accordance with the present invention.

FIG. 4 shows another embodiment of the ionic activity measuring device in accordance with the present invention. In this embodiment, the region surrounding the liquid feed holes 410' and 420' is formed as a recess 450' having a depth larger than the height of a bridge 600', and the bridge 600' is disposed in the recess 450' so as to contact the upper faces of the liquid feed holes 410' and 420'. Therefore, also in this embodiment, the bridge 600' does not project from the upper surface of an upper frame half 400'.

The configuration of the embodiment of FIG. 3 is similar to the configuration described above with reference to FIGS. 1, 2 and 3, except for the upper frame half 400'.

It should be understood that the aforesaid embodiments and the embodiments described below may be modified in various manners. For example, the positions of the ion selective electrode pairs and the porous liquid distributing members may be interchanged with each other, and the ion selective electrode pairs may be disposed with their ion selective layers facing up. In this case, the aforesaid liquid ascent passages act in the same manner as the liquid descent passages. Also, the water-impermeable member layer may be omitted.

Embodiments of the ionic activity measuring device in accordance with the present invention, wherein an end portion of at least one of the porous liquid distributing members is protruded to a part of a region under the corresponding liquid feed holes, whereby the fed solution is allowed to enter from the side face of said end portion, will hereinbelow be described with reference to FIGS. 5 to 10.

Figure 5:
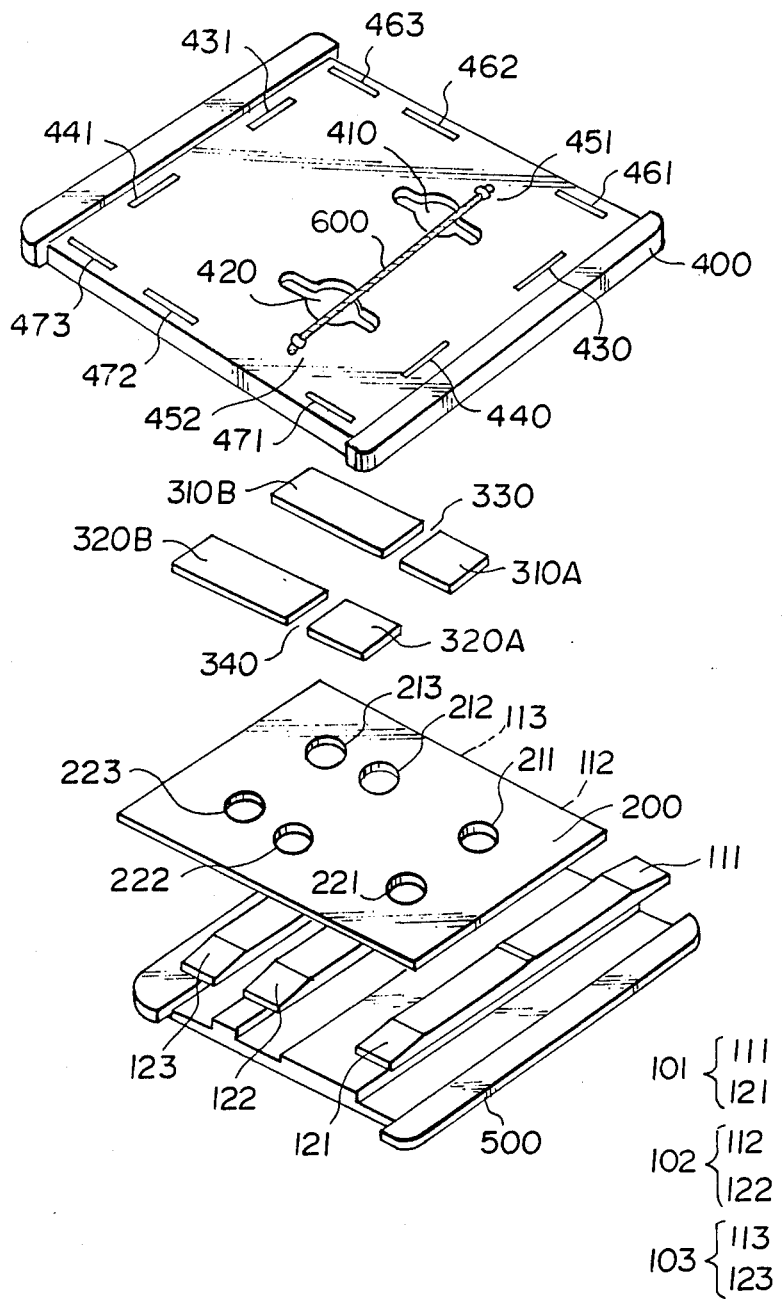
FIG. 5 is a perspective exploded view showing a further embodiment of the ionic activity measuring device in accordance with the present invention.
Figure 6:
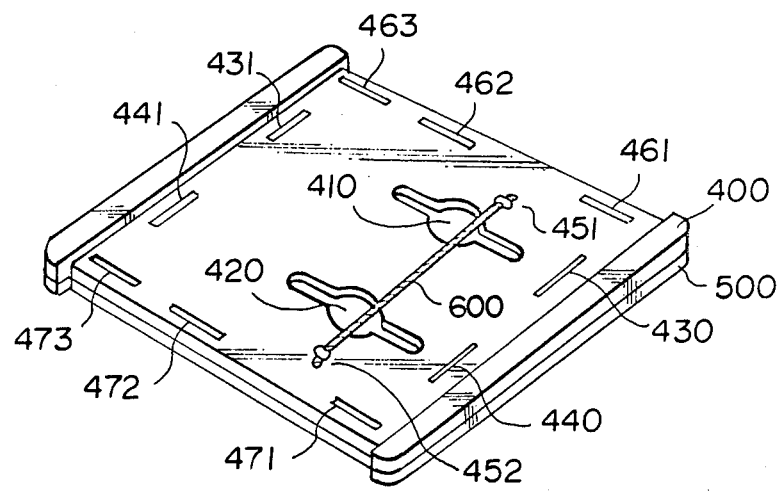
FIG. 6 is a perspective view showing the assembled form of the embodiment of FIG. 5.

In FIGS. 5 and 6 similar elements are numbered with the same reference numerals with respect to FIGS. 1 and 2. In this embodiment, a pair of porous liquid distributing members 310A and 310B are disposed to make liquid receiving holes 211, 212 and 213 (i.e. through holes extending respectively to the ion selective electrodes 111, 112 and 113) communicate with each other, and a pair of porous liquid distributing members 320A and 320B are disposed to make liquid receiving holes 221, 222 and 223 (i.e. through holes extending respectively to the ion selective electrodes 121, 122 and 123) communicate with each other. The porous liquid distributing members 310A and 310B are associated with the liquid feed hole 410, and the porous liquid distributing members 320A and 320B are associated with the liquid feed hole 420. The upper frame half 400 is provided with air discharging holes 430, 431, 440 and 441 for promoting liquid distribution through the porous liquid distributing members 310A, 310B, 320A and 320B, and measuring probe insertion holes 461, 462, 463, 471, 472 and 473 respectively communicating with the ion selective electrodes 111, 112, 113, 121, 122 and 123. The ends of the porous bridge 600 are secured at sections 451 and 452.

In the embodiment of FIG. 5, a reference solution fed to the liquid feed hole 410 permeates through the porous liquid distributing members 310A and 310B and is distributed to the liquid receiving holes 211, 212 and 213, and a sample solution fed to the liquid feed hole 420 permeates through the porous liquid distributing members 320A and 320B and is distributed to the liquid receiving holes 221, 222 and 223. Since the porous liquid distributing members 310A and 310B are separated at a space 330, and the porous liquid distributing members 320A and 320B are separated at a space 340, the fed solutions are fed from the spaces 330 and 340 to the side faces at the ends of the porous liquid distributing members 310A, 310B, 320A and 320B.

Figure 7:
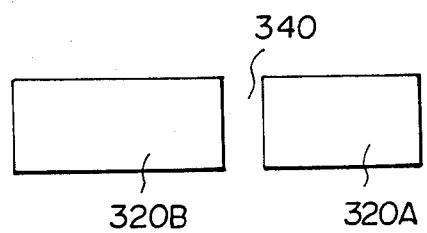
FIG. 7 is a plan view showing the porous liquid distributing members used in the embodiment of FIG. 5.

As shown in FIG. 7, the space 340 is disposed between the porous liquid distributing members 320A and 320B. Since the space 340 is narrower than the width of the liquid feed hole 420, the side faces at the ends of the porous liquid distributing members 320A and 320B are protruded to a part of the region under the liquid feed holes 420.

Figure 8:
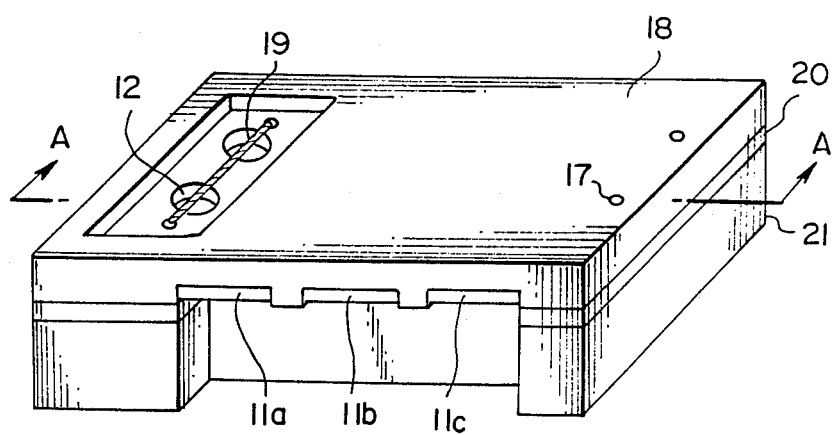
FIG. 8 is a perspective view showing a still further embodiment of the ionic activity measuring device in accordance with the present invention.
Figure 8A:
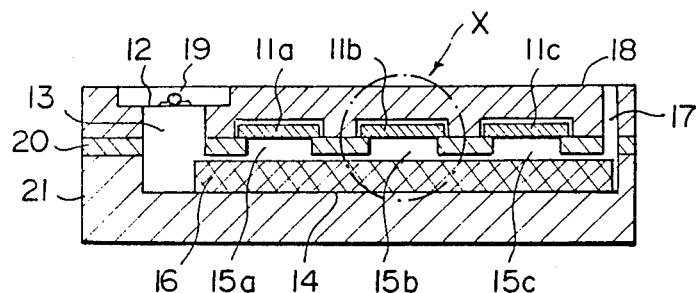
FIG. 8A is a sectional view taken along line A—A of FIG. 8.
Figure 8B:
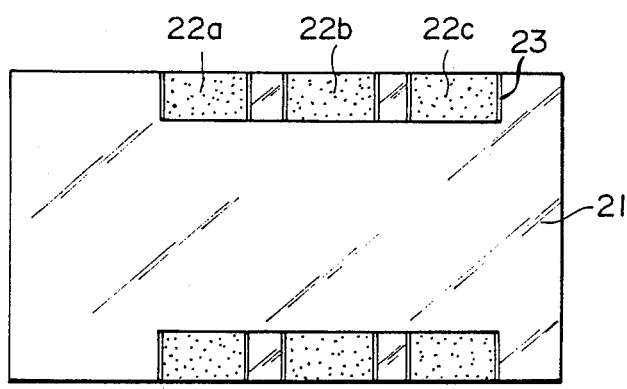
FIG. 8B is a bottom view of FIG. 8.
Figure 8C:
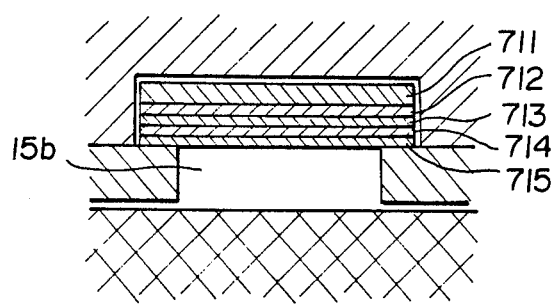
FIG. 8C is an enlarged view showing the section X surrounded by the circle in FIG. 8A.
Figure 9:
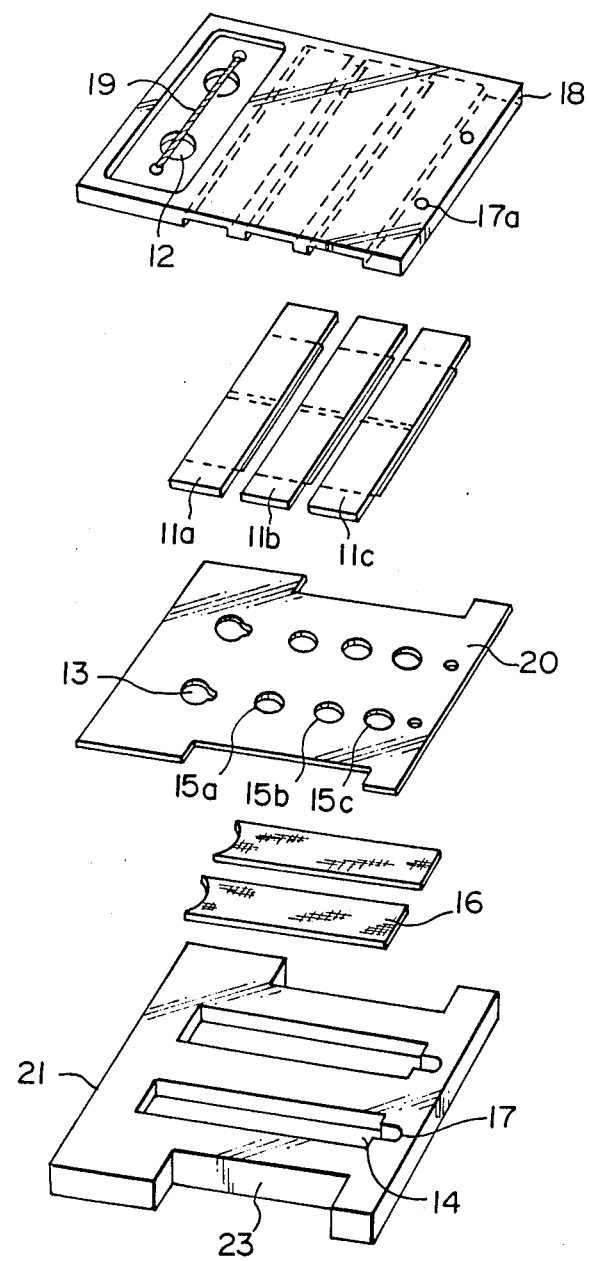
FIG. 9 is an exploded view showing the embodiment of FIG. 8.

In another embodiment shown in FIGS. 8, 8A, 8B, 8C and 9, ion selective electrode pairs 11a, 11b and 11c are disposed with their ion selective layers facing down. As shown in FIG. 8C, each of the sheet-like ion selective electrodes constituting each of the ion selective electrode pairs 11a, 11b and 11c comprises a supporting member 711 formed of a plastic sheet or the like, and a metallic silver deposited layer 712, a silver chloride layer 713, an electrolyte layer 714 and an ion selective layer 715 overlaid on the supporting member 711. The sheet-like ion selective electrode is disposed in the ionic activity measuring device with the supporting member 711 facing up.

As shown in FIG. 8A, the liquid applying section for applying the fed solution to the surfaces of the ion selective layers of the ion selective electrodes is constituted by a through hole 13, a horizontal passage 14 through which the solution advances horizontally to positions under the surfaces of the ion selective layers, and ascent passages 15a, 15b and 15c through which the solution advances up to the surfaces of the ion selective layers. A porous liquid distributing member 16 having fine continuous pores capable of giving rise to capillary attraction is housed in the horizontal passage 14. The porous liquid distributing member may be housed also in the ascent passages 15a, 15b and 15c.

At the leading end portion of the horizontal passage 14, an air discharging hole 17 is formed for making smooth the permeation of the solution.

The ion selective electrode pairs 11a, 11b and 11c are housed and secured in the upper frame half 18 formed of a plastic material. The upper frame half 18 is provided with liquid feed holes 12, 12, and a porous bridge 19 extends across the liquid feed holes 12, 12.

Regions of small protuberances (not shown) may be provided around the liquid feed holes 12, 12 to prevent the fed solutions from spreading outside the liquid feed holes 12, 12 and to use the regions as guides for facilitating the feeding of the solution and making the feeding reliable.

A sheet-like water-impermeable intermediate member (a plastic mask) 20 is disposed under the upper frame half 18. A part of the liquid descent passage 13 and the liquid ascent passages 15a, 15b and 15c are formed as openings through the sheet-like water-impermeable intermediate member 20. The water-impermeable intermediate member 20 is secured by a heat-sensitive adhesive to the lower surface of the upper frame half 18.

A lower frame half 21 formed of a plastic material is disposed under the sheet-like water-impermeable intermediate member 20.

The horizontal passage 14 is formed as a recess in the lower frame half 21. The porous liquid distributing member 16 is housed and secured in the horizontal passage 14 so that the end of the porous liquid distributing member 16 faces the through hole 13 and covers only a part of the bottom of the through hole 13.

As shown in FIG. 8B, at each of the side sections of the lower frame half 21, a cutaway region 23 is formed for exposing electrical connecting regions 22a, 22b and 22c of the ion selective electrodes 11a, 11b and 11c downwardly.

The lower frame half 21 is secured by a heat-sensitive adhesive to the lower surface of the water-impermeable intermediate member 20.

Figure 10:
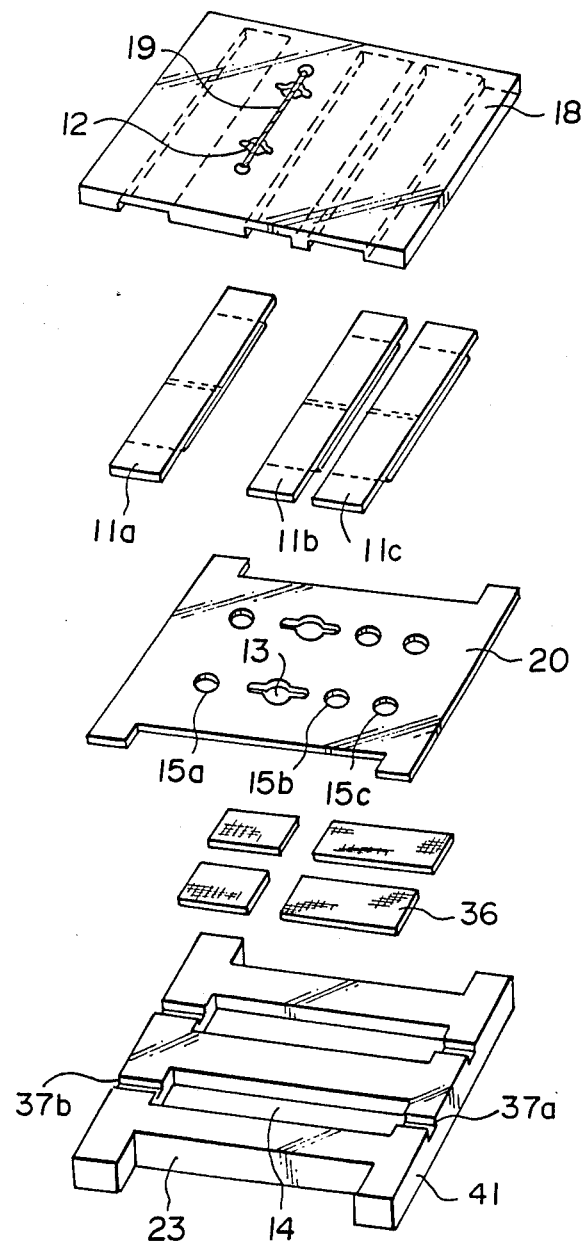
FIG. 10 is an exploded view showing an even further embodiment of the ionic activity measuring device in accordance with the present invention.

In a further embodiment shown in FIG. 10, the ion selective electrode pair 11a is disposed on the left side of the liquid feed holes 12, 12, and the ion selective electrode pairs 11b and 11c are disposed on the right side of the liquid feed holes 12, 12. With this configuration, the distance between the liquid feed holes 12, 12 and the farthest ion selective electrode pair is shorter than in the embodiment of FIG. 9. Therefore, this embodiment is advantageous for the case where a solution having high viscosity such as whole blood is used as the sample solution.

In the embodiment of FIG. 10, four porous liquid distributing members 36, 36, 36, 36 are disposed in the horizontal passages 14, 14 so that side faces at the ends of these members face the through holes 13, 13 and cover only a part of the bottoms of the through holes 13, 13. Also, since the three ion selective electrode pairs are distributed on both sides of the through holes 13, 13, air discharging grooves 37a and 37b are formed at opposite end portions of a lower frame half 41.

In the embodiments described with reference to FIGS. 5 to 10, the space between the porous liquid distributing members need not necessarily be formed for both sets of the porous liquid distributing members. Particularly, when the viscosity of the reference solution is low, it is only necessary that the space be provided between the porous liquid distributing members for distributing the sample solution, and a member of the type disclosed in Japanese Unexamined Patent Publication No. 58(1983)-211648 may be employed for the reference solution.

Embodiments of the ionic activity measuring device in accordance with the present invention, wherein the porous bridge extends through the pair of the liquid feed holes at positions deviated from the centers of the liquid feed holes, will hereinbelow be described with reference to FIGS. 11 to 15.

Figure 11:
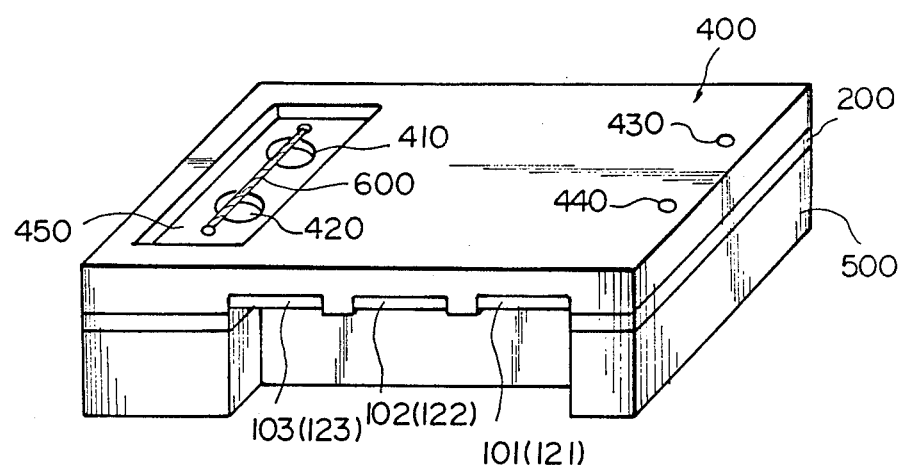
FIG. 11 is a perspective view showing another embodiment of the ionic activity measuring device in accordance with the present invention.
Figure 13:
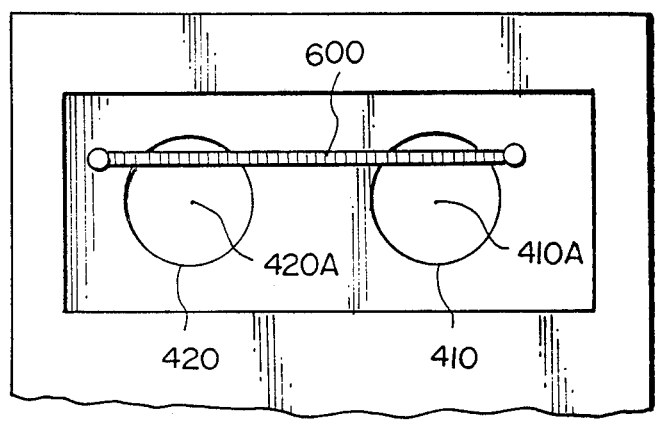
FIG. 13 is an enlarged plan view showing a part of the embodiment of FIG. 11.

In FIGS. 11 and 12, similar elements are numbered with the same reference numerals with respect to FIGS. 1 and 2. In this embodiment, the porous bridge 600 is disposed on the liquid feed holes 410 and 420 to extend therethrough at positions deviated from the centers thereof. As shown more clearly in FIG. 13, the bridge 600 is disposed to overlap a part of the circumferences of the liquid feed holes 410 and 420 approximately in parallel with a straight line on which centers 410A and 420A of the liquid feed holes 410 and 420 lie. Therefore, when a reference solution and a sample solution are applied to the liquid feed holes 410 and 420 by positioning ends of pipettes or the like in the vicinity of the centers 410A and 420A of the liquid feed holes 410 and 420, there is no risk of the fed solutions being repulsed by the bridge 600 and lost, and it is possible to prevent the ends of the pipettes or the like from coming into contact with the bridge 600 and damaging it. In this embodiment, since the region surrounding the liquid feed holes 410 and 420 and the bridge 600 is formed as the recess 450 in the upper frame half 400, it is possible to prevent the fed solutions from spilling out of the upper frame half 400, and to prevent the solutions from coming outside of the recess 450 even though the solutions are scattered.

Figure 15:
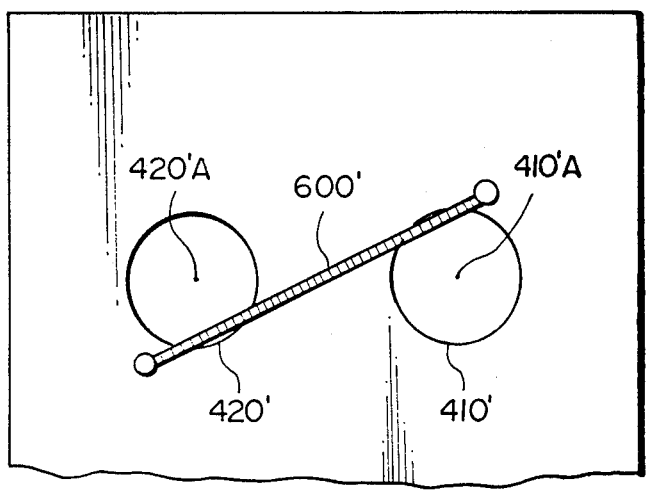
FIG. 15 is an enlarged plan view showing a part of the embodiment of FIG. 14, FIG. 16 and 17 are perspective views showing a still further embodiment of the ionic activity measuring device in accordance with the present invention, as viewed from above and below the device.
Figure 14:
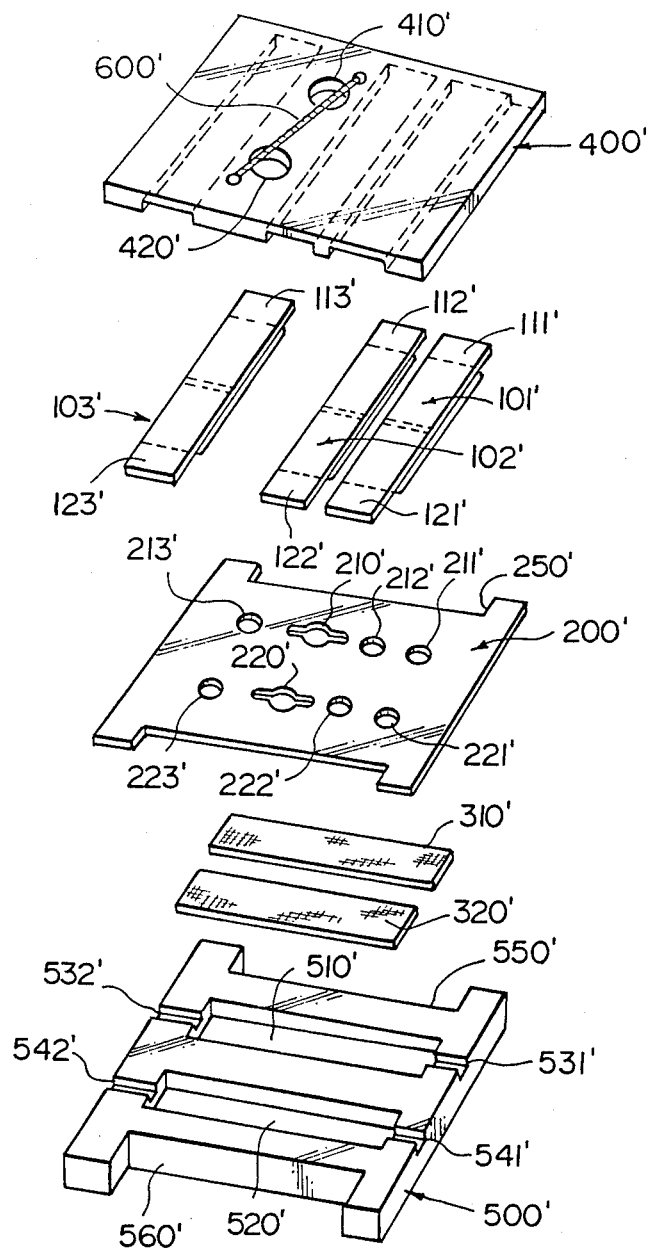
FIG. 14 is a perspective exploded view showing a further embodiment of the ionic activity measuring device in accordance with the present invention.

In another embodiment shown in FIGS. 14 and 15, an ion selective electrode pair 103' is disposed on one side and ion selective eletrode pairs 101' and 102' are disposed on the other side with respect to liquid feed holes 410' and 420'. As mentioned above, this configuration is advantageous particularly for the case where the sample solution has high viscosity much as whole blood. In this embodiment, a bridge 600' is disposed obliquely to overlap a part of the circumferences of the liquid feed holes 410' and 420' at positions deviated from centers 410'A and 420'A. Also, air discharging grooves 531', 532', 541' and 542' are formed as through holes extending to the side faces of the lower frame half 500'.

Figure 16:
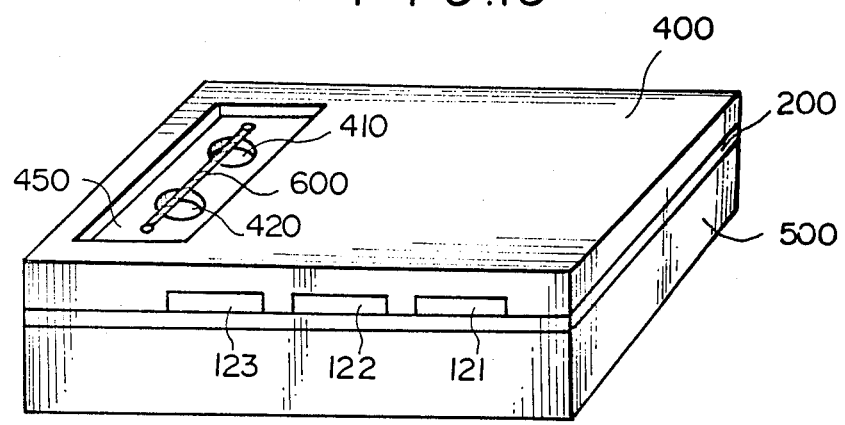
Figure 17:
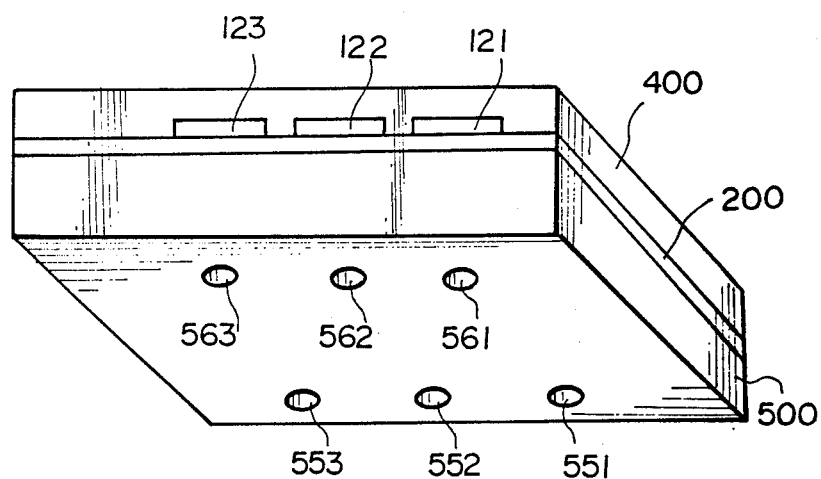
Figure 18:
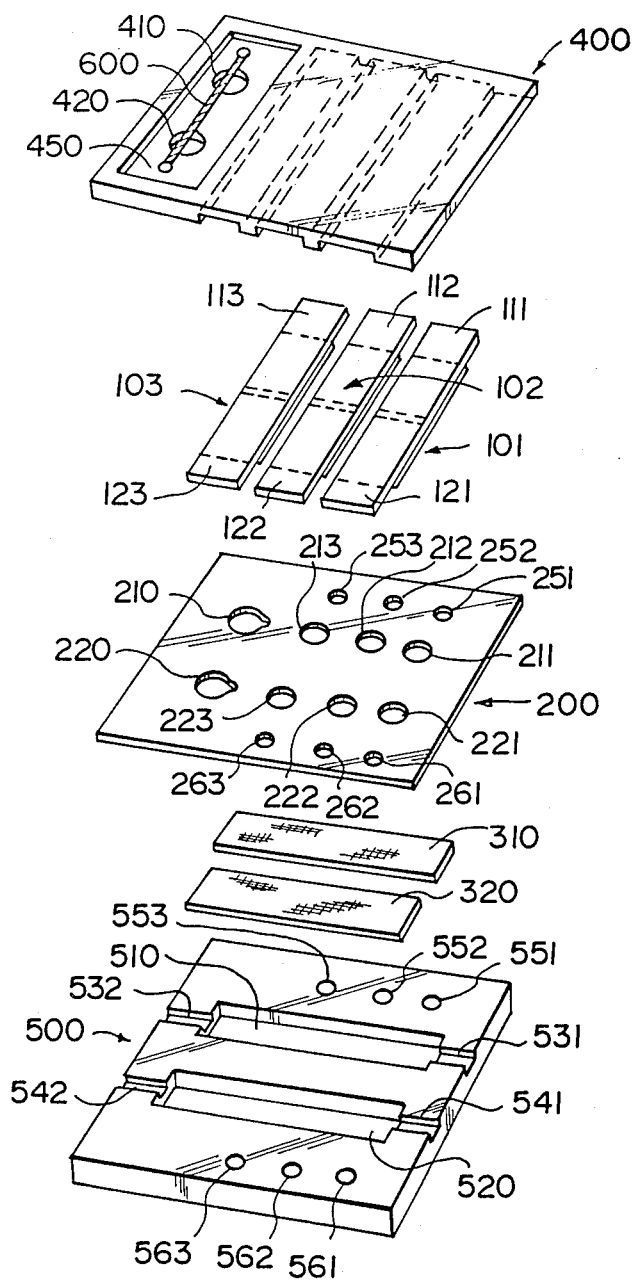
FIG. 18 is a perspective exploded view showing the embodiment of FIG. 16.

A further embodiment will hereinbelow be described with reference to FIGS. 16, 17 and 18. In FIGS. 16, 17 and 18, similar elements are numbered with the same reference numerals with respect to FIGS. 1 and 2. In this embodiment, the porous bridge 600 extends at positions deviated from the centers of the liquid feed holes 410 and 420, and the water-impermeable member layer 200 is provided with through holes 251, 252, 253, 261, 262 and 263 for insertion of potential measuring probes.

The lower frame half 500 is provided with vertical through holes 551, 552, 553, 561, 562 and 563 for probe insertion at positions respectively facing the through holes 251, 252, 253, 261, 262 and 263 perforated for insertion of potential measuring probes in the water-impermeable member layer 200. Also, a pair of air discharging grooves 531 and 532 and a pair of air discharging grooves 541 and 542 are formed at opposite ends of the recesses 510 and 520 in the lower frame half 500. The terminal sections at opposite ends of the ion selective electrode pairs 101, 102 and 103 disposed with their ion selective layers facing down are partially exposed to the lower surface of the ionic activity measuring device through the probe insertion through holes 251, 252, 253, 261, 262 and 263 of the water-impermeable member layer 200, and the probe insertion through holes 551, 552, 553, 561, 562 and 563 of the lower frame half 500.

Figure 19:
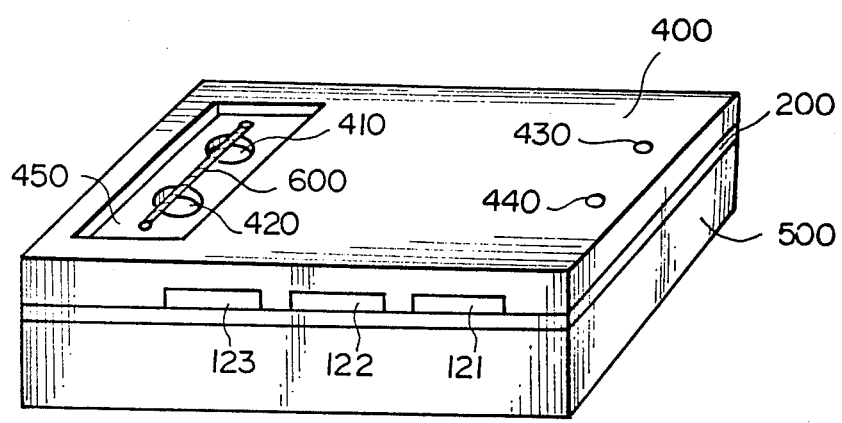
FIG. 19 is a perspective view showing still another embodiment of the ionic activity measuring device in accordance with the present invention.
Figure 20:
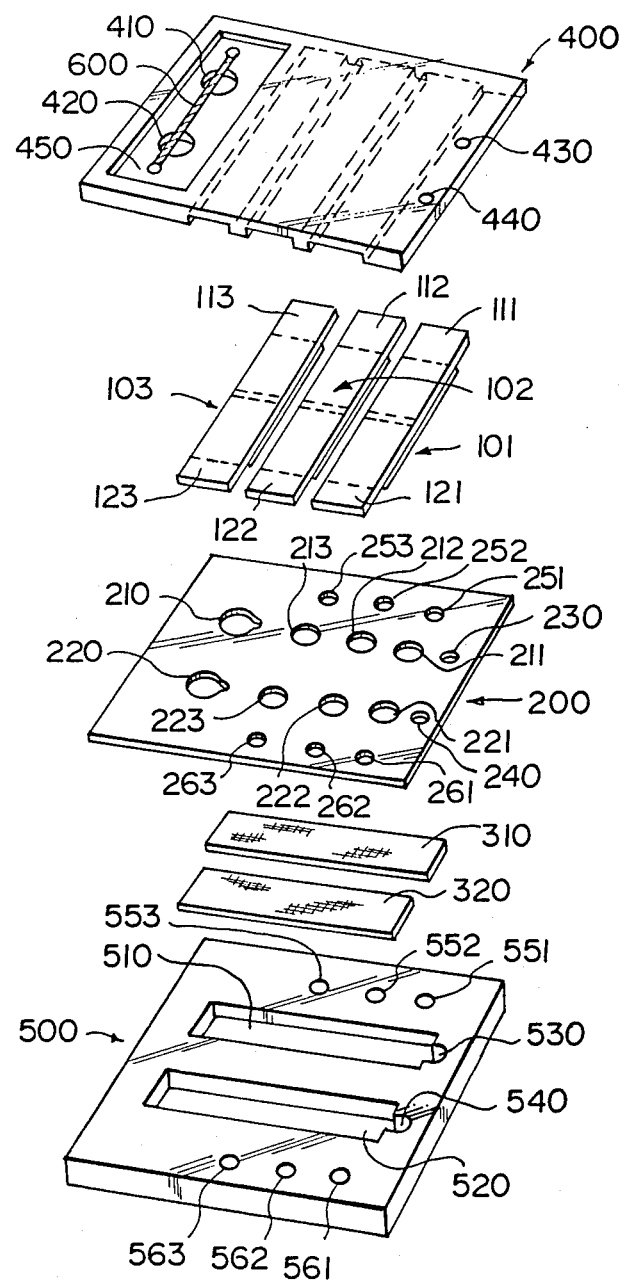
FIG. 20 is a perspective exploded view showing the embodiment of FIG. 19.

Still further embodiments will now be described with reference to FIGS. 19 to 22. The embodiment shown in FIGS. 19 and 20 is similar to the embodiment described above with reference to FIGS. 16, 17 and 18 except that, instead of the air discharging grooves 531, 532, 541 and 542, a pair of the through holes (air discharging holes) 430 and 440 are formed through the upper frame half 400, a pair of the through holes 230 and 240 are formed through the water-impermeable member layer 200, and a pair of air discharging holes 530 and 540 are formed in the lower frame half 500 so as to constitute air discharging holes extending through the whole ionic activity measuring device and open to the exterior at the upper surface of the upper frame half 400. The shapes of the air discharging holes 530 and 540 are adjusted to be smaller than the sizes of the recesses 510 and 520, so that the contact area of the lower frame half 500 with the water-impermeable member layer 200 does not become too small while maintaining the air discharging effects. For the same reasons, the sizes of the air discharging holes 430, 440, 230 and 240 are adjusted to be small. The air discharging holes 430, 440, 230, 240, 530 and 540 act to increase the permeation speed of the reference solution and the sample solution through the porous liquid distributing members 310 and 320, shorten the time taken for the solutions to arrive at the ion selective layers, and achieve solution feeding to the electrode surfaces without air confinement.

Figure 21:
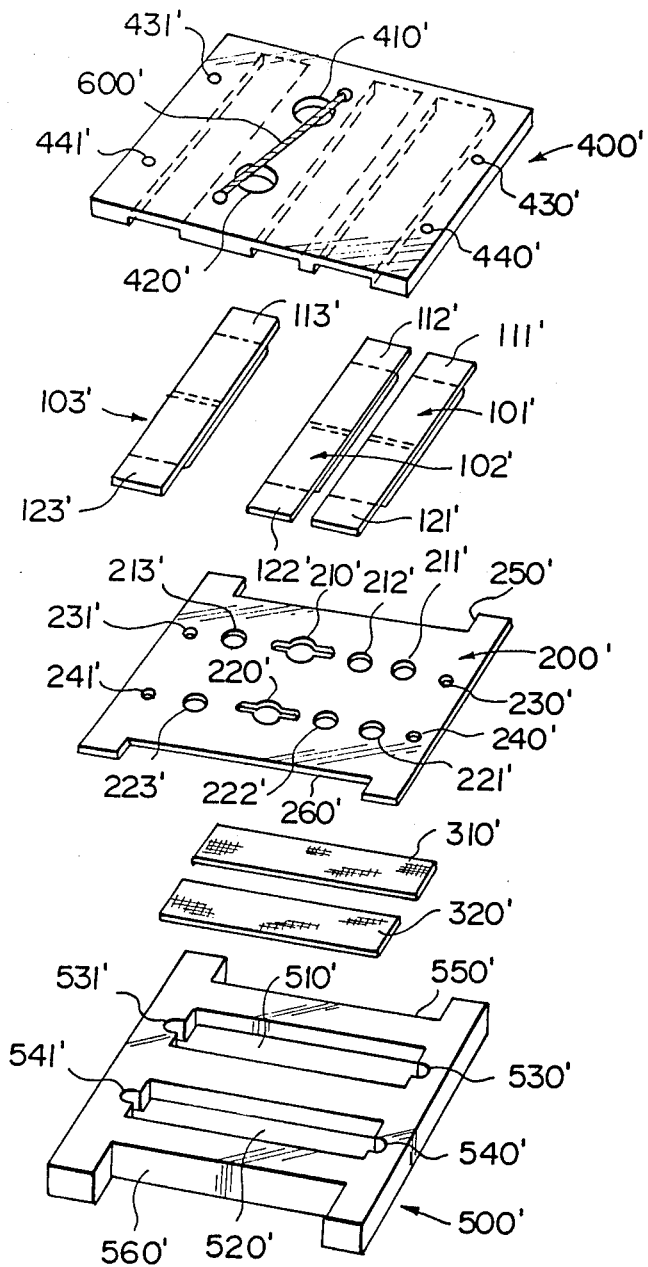
FIG. 21 is a perspective exploded view showing a further embodiment of the ionic activity measuring device in accordance with the present invention.

In the embodiment shown in FIG. 21, since the reference solution and the sample solution fed to liquid feed holes 410' and 420' must be distributed to the right and left, air discharging holes 530', 531' are formed at opposite ends of a recess 510' for housing a liquid distributing member 310', and air discharging holes 540' and 541' are formed at opposite ends of a recess 520' for housing a liquid distributing member 320'. Also, air discharging holes 430', 431', 440' and 441', and air discharging holes 230', 231', 240' and 241' are formed in an upper frame half 400' and a water-impermeable member layer 200' at positions corresponding to the air discharging holes 530', 531', 540' and 541' of a lower frame half 500'. Also, in this embodiment, a pair of cutaway regions 250' and 260' are formed on opposite sides of the water-impermeable member layer 200', and cutaway regions 550' and 560' are formed on opposite sides of the lower frame half 500' for exposing the terminal sections of ion selective electrode pairs 101', 102' and 103' downwardly to allow them to contact with potential measuring probes inserted from below.

Figure 22:
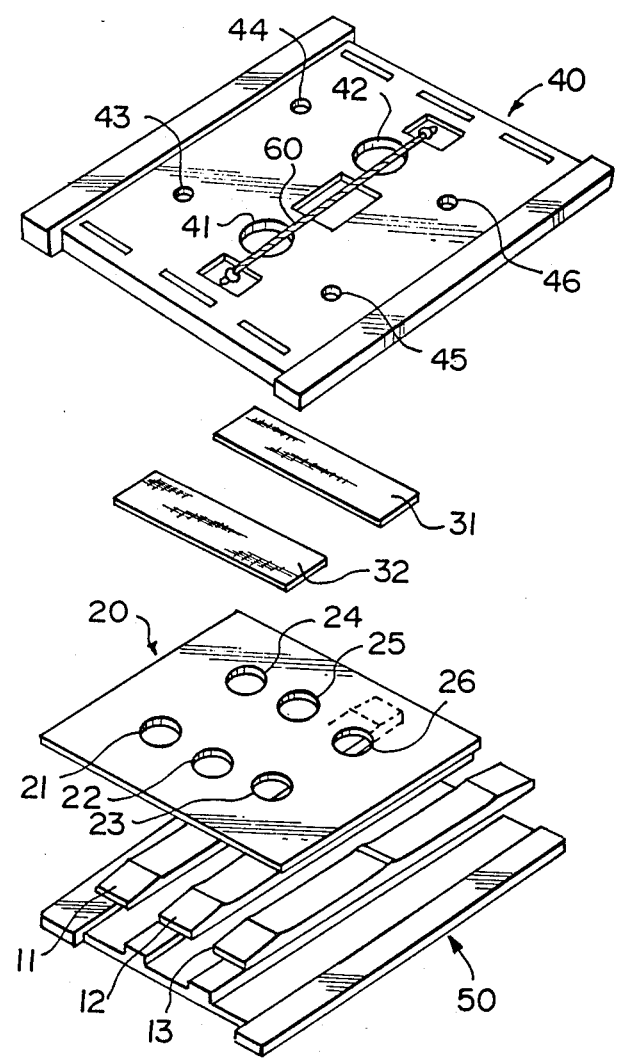
FIGS. 22 and 23 are perspective exploded views showing still further embodiments of the ionic activity measuring device in accordance with the present invention.

In the embodiment of FIG. 22, ion selective electrodes pairs 11, 12 and 13 are supported on a lower frame half 50, and porous liquid distributing members 31 and 32 are supported on an upper frame half 40. A water-impermeble member layer 20 sandwiched between the upper frame half 40 and the lower frame half 50 is provided with liquid descent passages 21, 22, 23, 24, 25 and 26, so that the reference solution and the sample solution fed to liquid feed holes 41 and 42 and permeating through the porous liquid distributing members 31 and 32 pass through the liquid descent passages 21, 22, 23, 24, 25 and 26 to the ion selective layers of the ion selective electrode pairs 11, 12 and 13. Air discharging holes 43, 44, 45 and 46 are formed through the upper frame half 40 at positions corresponding to both ends of the porous liquid distributing members for increasing the permeation speeds of the reference solution and the sample solution through the porous liquid distributing members 31 and 32.

Further embodiments of the ionic activity measuring device in accordance with the present invention, wherein a pair of liquid feed holes are disposed near the center between an ion selective electrode pair at one end and an ion selective electrode pair adjacent thereto, and said adjacent ion selective electrode pair is constituted by a potassium ion selective electrode pair, will hereinbelow be described with reference to FIGS. 5, 6 and 23. In the embodiment having the configuration as shown in FIGS. 5 and 6, the ion selective electrode pairs 101, 102 and 103 are disposed to stand side by side along the porous liquid distributing members 310A, 310B, 320A and 320B. The liquid feed holes 410 and 420 are disposed nearly at the center between the ion selective electrode pair 101 at one end and the ion selective electrode pair 102 at the middle. The middle electrode pair 102 is constituted by a K+ ion selective electrode pair, and the end electrode pairs 101 and 103 are constituted by, for example, a Na+ ion selective electrode pair and a Cl− ion selective electrode pair. Since the middle electrode pair 102, i.e. the electrode pair nearest to the liquid feed holes 410 and 420 and adjacent to the end electrode pair 101, is constituted by a K+ ion selective electrode pair, it is possible to measure the K+ ionic activity more accurately than with the other configuration as will be described in detail later.

Figure 23:
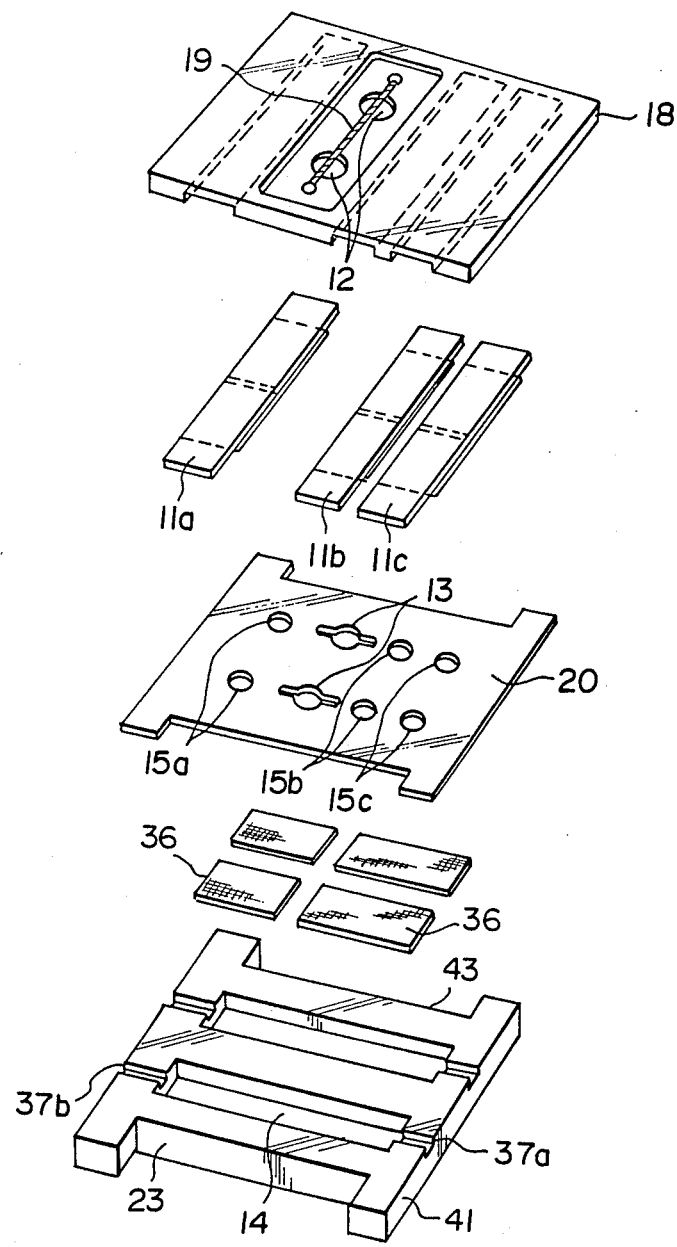

FIGS. 23 shows an embodiment having the configuration similar to the configuration of FIG. 10. In FIG. 23, similar elements are numbered with the same reference numerals with reference to FIG. 10. Also in this embodiment, the middle ion selective electrode pair 11b is constituted by a K+ ion selective electrode pair, and it is possible to accurately measure the K+ ionic activity. This embodiment may be modified so that the upper frame half 18, the lower frame half 41, the intermediate member 20, and the liquid distributing members 36, 36 may be extended to provide a fourth electrode pair, for example, a carbonate ion selective electrode pair, adjacent to the electrode pair 11c.

Measurement Example

Blood plasma samples were obtained from three blood specimens in accordance with the conventional method. A part of each specimen was maintained as whole blood.

In the ionic activity measuring device as shown in FIG. 23, the ion selective electrode pairs 11a, 11b and 11c were constituted by the same K+ (potassium) ion selective electrode pairs. To the liquid feed holes 12, 12, 40 µl portions of a reference solution and one of the whole blood or blood plasma samples were fed, differences in potential were measured, and the K+ ion concentrations were calculated from a calibration curve drawn by use of control blood serum. The K+ ion concentrations obtained from the three potassium ion selective electrode pairs at different positions were as shown below. The unit of the K+ ion concentration is meq/l.

|  |  | Electrode pair | | |
|---|---|---|---|---|
|  |  | 11a | 11b | 11c |
| Blood specimen 1 | Whole blood | 4.28 | 3.96 | 4.36 |
|  | Blood plasma | 3.96 | 3.98 | 4.02 |
| Blood specimen 2 | Whole blood | 4.57 | 4.49 | 4.52 |
|  | Blood plasma | 4.78 | 4.54 | 4.82 |
| Blood specimen 3 | Whole blood | 4.94 | 4.94 | 4.97 |
|  | Blood plasma | 5.16 | 4.84 | 5.26 |

The measured values for the blood plasma samples were within the experiment error range for every electrode pair. The measured values for the whole blood samples were slightly different among the electrode pairs. For the electrode pair 11b, the measured values for the whole blood samples were approximately identical with the concentrations for the blood plasma samples. On the other hand, for the electrode pairs 11a and 22c, the measured values for the whole blood samples were larger by 0.2 to 0.4 meq/l than the values for the blood plasma samples.

The obtained results indicate that hemolysis arises with the whole blood samples containing blood corpuscles and K+ ion concentrations higher than in the blood plasma samples are detected with the electrode pairs 11a and 11c. On the other hand, at the electrode pair 11b, no hemolysis arises with the whole blood samples, and K+ ion concentrations identical with those in the blood plasma samples are detected. This difference arises though the electrode pairs 11a and 11b are at nearly equal distances from the liquid feed holes 12, 12, and therefore the time taken for the whole blood sample to arrive at the electrode pair 11a is approximately equal to the time taken for the whole blood sample to arrive at the electrode pair 11b. This is considered to be because the electrode pair 11c is present on the side outward of the electrode pair 11b, the porous liquid distributing members 36, 36 are extended via the electrode pair 11b up to the electrode pair 11c, and therefore hemolysis does not readily arise at the electrode pair 11b.

I claim:

1. In an ionic activity measuring device comprising:
   (i) at least three pairs of sheet-like ion selective electrodes provided with ion selective layers on their surfaces and electrically isolated from each other,
   (ii) at least one pair of porous liquid distributing members for feeding a reference solution and a sample solution respectively to said ion selective layers of said ion selective electrodes,
   (iii) a frame for housing said ion selective electrodes and said porous liquid distributing members therein and provided with a pair of liquid liquid feed holes respectively disposed above said porous liquid distributing members for feeding said reference solution and said sample solution independently of each other to said porous liquid distributing members, and (iv) a porous bridge for achieving electrical conduction between said reference solution and said sample solution fed to said pair of the liquid feed holes, said at least three pairs of the sheet-like ion selective electrodes being disposed to stand side by side along said porous liquid distributing members, the improvement which comprises said pair of the liquid feed holes being disposed in the vicinity of the center between the ion selective electrode pair positioned at one end and the ion selective electrode pair adjacent to said ion selective electrode pair positioned at said one end, said ion selective electrode pair adjacent to said ion selective electrode pair positioned at said one end, being a potassium ion selective electrode pair.

2. A device as defined in claim 1 wherein said frame comprises an upper frame half for supporting said ion selective electrodes therein and provided with said pair of the liquid feed holes for feeding said reference solution and said sample solution independently of each other to said porous liquid distributing members, and a lower frame half for supporting said porous liquid distributing members therein.

3. A device as defined in claim 1 wherein said frame comprises an upper frame half for supporting said porous liquid distributing members therein and provided with said pair of the liquid feed holes for feeding said reference solution and said sample solution independently of each other to said porous liquid distributing members, and a lower frame half for supporting said ion selective electrodes.

4. A device as defined in claim 1 wherein said porous bridge is disposed in a recess formed in the surface of said frame, and the depth of said recess is adjusted to a value not smaller than the height of said porous bridge.

5. The device as defined in claim 1 wherein an end portion of each of said porous liquid distributing members protrudes to a region under the corresponding liquid feed hole, whereby a reference or sample solution can enter from the side face of said end portion.

* * * * *